(12) United States Patent
Gilmartin et al.

(10) Patent No.: US 8,354,474 B2
(45) Date of Patent: Jan. 15, 2013

(54) CROSS-LINKING COMPOUND

(75) Inventors: Brian Gilmartin, Williamsville, NY (US); Liang-Bih Lin, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 818 days.

(21) Appl. No.: 12/509,370

(22) Filed: Jul. 24, 2009

(65) Prior Publication Data

US 2011/0021714 A1 Jan. 27, 2011

(51) Int. Cl.
*C08C 19/24* (2006.01)
*C07F 9/02* (2006.01)
*C08G 63/91* (2006.01)

(52) U.S. Cl. .......... 525/340; 525/418; 525/538; 568/12

(58) Field of Classification Search ............... 525/340, 525/418, 538; 568/12
See application file for complete search history.

(56) References Cited

U.S. PATENT DOCUMENTS 5,157,446 A 10/1992 Kusaka
5,602,270 A * 2/1997 Odello et al. ................ 558/80

OTHER PUBLICATIONS

Richards et al. ("In situ complexation of lithium chloride by amphiprotic cyclophosphazenes", Chem. Comm., May 2003, p. 1392 and 1393; referenced as Richards hereinafter).*
U.S. Patent Application entitled: Cross-Linked Protective Outer Coating, Gilmartin, et al., 20 pages.
Richards et al.: Chem. Commun., 2003, pp. 1392-1393, XP002618207, *compound (1a)* *p. 1392, col. 1, line 9-line 14* *abstract*.
EP Search Report dated Jan. 31, 2011, EP Serial No. 10169847.0, 6 pages.

* cited by examiner

*Primary Examiner* — Ling Choi
*Assistant Examiner* — Chun-Cheng Wang
(74) *Attorney, Agent, or Firm* — Pillsbury Winthrop Shaw Pittman LLP (57) ABSTRACT

The presently disclosed embodiments are directed generally to a composition that forms a cross-linked protective outer coating or layer able to withstand high temperatures and which maintains integrity in such conditions. The protective coating may be used in imaging apparatus members and components, for use in electrostatographic, including digital, apparatuses. Particular embodiments pertain to a fuser component having an outer coating comprised of a cross-linking composition that improves resistance to thermal degradation and extends the service life of the fuser component.

17 Claims, 4 Drawing Sheets

CROSS-LINKING COMPOUND

CROSS REFERENCE TO RELATED APPLICATIONS

Reference is made to commonly owned and co-pending, U.S. patent application Ser. No. 12/509,393 to Kim et al., filed the same day as the present application, entitled, "Cross-Linked Protective Outer Coating", the entire disclosures of which are incorporated herein by reference in its entirety.

BACKGROUND

The presently disclosed embodiments relate generally to a composition that forms a cross-linked protective outer coating or layer that withstands high temperatures and which maintains integrity in such conditions. The protective coating may be used in a variety of industries that require flame or heat resistant materials. The coating may form a layer on a variety of components that need to withstand high and degrading temperatures. For example, the protective coating may be used as insulating tapes for coating thermoplastic automobile accessories. In addition, the protective coating may also be used in xerographic components, such as, fuser components, photoreceptor components, and the like. In embodiments, the coating is used in imaging apparatus members and components, for use in electrostatographic, including digital, apparatuses. More particularly, the present embodiments pertain to a fuser component having an outer coating comprised of a cross-linking composition that improves resistance to thermal degradation and extends the service life of the fuser component. In other embodiments, the outer coating comprising the cross-linking composition is incorporated as an outer protective layer in various other imaging apparatus members or components that operate under high temperature conditions.

The components, including pressure components, fuser components, donor components, and heating components, and the like, are useful for many purposes including fixing a toner image to a copy substrate. In a specific embodiment, there is provided a fuser member comprising a protective outer coating or layer. In embodiments, the outer layer is positioned on a substrate, which may be of many configurations including a roller, belt, film, or like substrate. In other embodiments, the outer layer has an outer release layer thereon. In further embodiments, there is positioned between the substrate and the outer layer, an intermediate and/or adhesive layer. The present invention may be useful as fuser members in xerographic machines, including color machines.

In a typical electrostatographic reproducing apparatus, a light image of an original to be copied is recorded in the form of an electrostatic latent image upon a photosensitive member and the latent image is subsequently rendered visible by the application of electroscopic thermoplastic resin particles which are commonly referred to as toner. The visible toner image is then in a loose powdered form and can be easily disturbed or destroyed. The toner image is usually fixed or fused upon a support, which may be the photosensitive member itself, or other support sheet such as plain paper.

The use of thermal energy for fixing toner images onto a support member is well known and methods include providing the application of heat and pressure substantially concurrently by various means, a roll pair maintained in pressure contact, a belt member in pressure contact with a roll, a belt member in pressure contact with a heater, and the like. Heat may be applied by heating one or both of the rolls, plate members, or belt members. With a fixing apparatus using a thin film in pressure contact with a heater, the electric power consumption is small, and the warming-up period is significantly reduced or eliminated.

It is important in the fusing process that the materials used or incorporated into the fuser components can withstand high temperatures and are resistant to thermal degradation as such components operate in and/or generate high heat.

Known fuser coatings include high temperature polymers such as polytetrafluoroethylene, perfluoroalkoxy, fluorinated ethylene propylene, silicone rubber, fluorosilicone rubber, fluoroelastomers, and the like. However, these coatings do not tend to stay clean during use. Further, the coatings often wear during use and/or become scratched during operation. In addition, these known surfaces often react with the toner, oil or debris from media, which causes the surface to become dirty and/or contaminated. The surface can, in turn, become physically damaged and results in a fuser member having a reduced useful function and short life.

Therefore, a need remains for fuser components for use in electrostatographic machines that have superior mechanical properties, including high resistance to thermal degradation. In addition, a need remains for prolonging fuser component service life despite the harsh operating conditions.

SUMMARY

According to aspects illustrated herein, there is provided a compound having the following structure:

wherein $R_i$ and $R_{ii}$ are independently selected alkyl groups or derivatives thereof.

Another embodiment provides a composition comprising a resin, an acid catalyst and a compound having the following structure:

wherein $R_i$ and $R_{ii}$ are independently selected alkyl groups or derivatives thereof.

Yet another embodiment, there is provided a composition comprising a resin cross-linked with a compound having the following structure:

wherein $R_i$ and $R_{ii}$ are independently selected alkyl groups or derivatives thereof.

BRIEF DESCRIPTION OF THE DRAWINGS

For a better understanding, reference may be made to the accompanying figures.

DETAILED DESCRIPTION

In the following description, reference is made to the accompanying drawings, which form a part hereof and which illustrate several embodiments. It is understood that other embodiments may be used and structural and operational changes may be made without departure from the scope of the present disclosure.

The presently disclosed embodiments are directed generally to a protective outer coating or layer comprising a novel composition that facilitates a high degree of cross-linking such that the resulting outer layer is highly resistant to thermal degradation. The outer coating comprises a phosphonitrilic trimer and film-forming resin which cross-link in the presence of an acid catalyst to form a coating that is able to remain intact in temperatures that known coating compositions could not. The coating may form a layer on a variety of components that need to withstand high and degrading temperatures. In the present embodiments, the protective coating may be used in xerographic components, such as, fuser components, photoreceptor components, and the like. In particular embodiments, the protective coating is provided as an outer layer of fuser components, such as a fuser member. Such fuser members exhibit improved wear resistance and life extension.

Inorganic polymers comprised of phosphonitrilic compounds have been studied as alternatives to organic polymers. Phosphonitrilic polymers offer a relatively simplistic means of achieving structure-function relationship, which generates a broader range of physical properties compared to organic materials. Phosphonitrilic polymers have desirable properties (e.g., thermal resistance, electrical properties, hydrophobicity/hydrophilicity, biomedical applications, and the like) which can be tailored through syntheses based on the side chain groups of the respective monomer(s).

The present embodiments are based upon cross-linking a new phosphonitrilic trimer with a film-forming resin to form a protective coating. The phosphonitrilic trimer has six alkoxyalkyl linkages and, in the presence of an acid catalyst, is able to cross-link with the resin to form a coating that is highly resistant to thermal degradation. In particular embodiments, the acid catalyst is selected from the group consisting of p-toluenesulfonic acid, dinonylnaphthalenesulfonic acid, dinonylnaphthalenedisulfonic acid, dodecylbenzenesulfonic acid, and the like and mixtures thereof. The new coating of the present embodiments demonstrate complete improved thermal stability (e.g., complete decomposition at temperatures of greater than 800° C. by thermogravimetric analysis), substantially higher than typically seen from organic resins such as melamine and polyol which generally degrade at about 600° C. In addition, the coating exhibits excellent resistance against concentrated acids and is also harder than several commercially available polymers, such as high and low density polyethylene and polystyrene.

As discussed above, the phosphonitrilic trimer prepared with six alkoxyalkyl groups. It has structural features that are similar to commercially available melamines (such as hexamethoxymethylmelamine, Cymel 303 available from Cytec Industries Inc. (West Paterson, N.J.)), but with twice the potential cross-linking amino groups. In the presence of an acid catalyst, the phosphonitrilic trimer cross-links with a film-forming resin. This is similar to the reaction that some melamines have in which the melamines cross-link, in the presence of an acid catalyst, with hydroxyl-, carboxyl-, and/or amide containing compounds through alkoxy linkages. The phosphonitrilic trimer has the following structure:

wherein $R_i$ and $R_{ii}$ are independently selected alkyl groups or derivatives thereof.

In embodiments, the the phosphonitrilic trimer has a molecular weight (Mw) of from about 300 to about 900 g/mol, or from about 500 to about 700 g/mol. The phosphonitrilic trimer compound may be in gelatinous form and is miscible in organic solvents.

In further embodiments, the phosphonitrilic trimer is present in the outer coating or layer in an amount of from about 5 percent to about 95 percent, or from about 50 percent to about 75 percent by weight of the total weight of the outer coating or layer. In other embodiments, the film-forming resin is present in the outer coating or layer in an amount of from about 5 percent to about 95 percent, or from about 25 percent to about 50 percent by weight of the total weight of the outer coating or layer. In embodiments, a ratio of the phosphonitrilic trimer to the resin in the outer layer is from about 0.5 to about 3. In embodiments, the film-forming resin can be selected from, but are not limited to, thermoplastic and thermosetting resins such as polycarbonates, polyesters, polyurethanes, polystyrenes, polyarylethers, polyarylsulfones, polysulfones, polyethersulfones, polyphenylene sulfides, polyvinyl acetate, polyacrylates, polyvinyl acetals, polyamides, polyimides, amino resins, phenolic resins, phenoxy resins, epoxy resins, phenylene oxide resins, polystyrene and acrylonitrile copolymers, vinyl acetate copolymers, acrylate copolymers, alkyd resins, styrene-butadiene copolymers, styrene-alkyd resins, polyvinylcarbazole, and the like, and mixtures thereof. In particular embodiments, the resin may be selected from the group consisting of acrylic polyol, polyether polyol, polyester polyol, and the like and mixtures thereof. In further embodiments, the protective outer coating or layer has a thickness of from about 0.1 to about 50 μm, or from about 5 to about 40 μm.

The exemplary embodiments of this disclosure are described below with reference to the drawings. The specific terms are used in the following description for clarity, selected for illustration in the drawings and not to define or limit the scope of the disclosure. The same reference numerals are used to identify the same structure in different figures unless specified otherwise. The structures in the figures are not drawn according to their relative proportions and the drawings should not be interpreted as limiting the disclosure in size, relative size, or location. In addition, though the discussion will address negatively charged systems, the imaging members of the present disclosure may also be used in positively charged systems. The present invention is directed to fuser components, and in particular, fusing components including fuser members, pressure members, donor members, external heat members, and other like components that operate in and/or generate high temperatures. In embodiments, the fuser member can be a pressure belt, fuser roller, fusing belt, pressure roller, and the like.

In an embodiment of the present invention, the fuser component comprises a substrate and a protective outer layer comprising a phosphonitrilic timer cross-linked with a film-forming resin. In other embodiments, the fuser component comprises a substrate having the protective outer layer and an outer release layer disposed on the protective outer layer. In yet other embodiments, optional adhesive and/or intermediate layers can be present between the substrate and the protective outer layer, and/or between the protective outer layer and the outer release layer.

Figure 1:
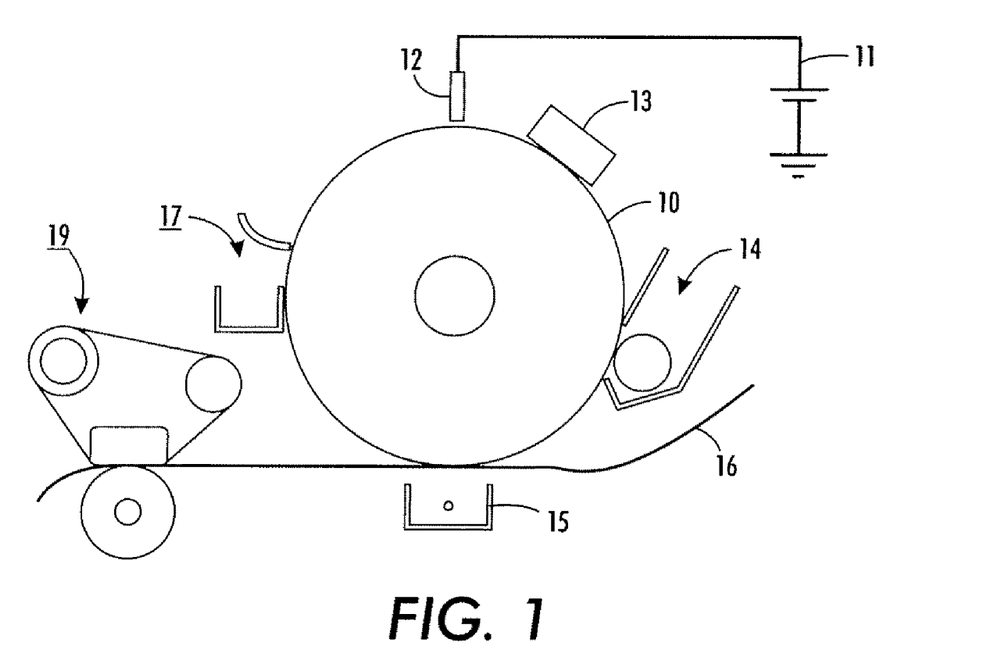
FIG. 1 is an illustration of a general electrostatographic apparatus.

Referring to FIG. 1, in a typical electrostatographic reproducing apparatus, a light image of an original to be copied is recorded in the form of an electrostatic latent image upon a photosensitive member and the latent image is subsequently rendered visible by the application of electroscopic thermoplastic resin particles which are commonly referred to as toner. Specifically, photoreceptor 10 is charged on its surface by means of a charger 12 to which a voltage has been supplied from power supply 11. The photoreceptor is then imagewise exposed to light from an optical system or an image input apparatus 13, such as a laser and light emitting diode, to form an electrostatic latent image thereon. Generally, the electrostatic latent image is developed by bringing a developer mixture from developer station 14 into contact therewith.

Development can be effected by use of a magnetic brush, powder cloud, or other known development process. A dry developer mixture usually comprises carrier granules having toner particles adhering triboelectrically thereto. Toner particles are attracted from the carrier granules to the latent image forming a toner powder image thereon. Alternatively, a liquid developer material may be employed, which includes a liquid carrier having toner particles dispersed therein. The liquid developer material is advanced into contact with the electrostatic latent image and the toner particles are deposited thereon in image configuration.

After the toner particles have been deposited on the photoconductive surface, in image configuration, they are transferred to a copy sheet 16 by transfer means 15, which can be pressure transfer or electrostatic transfer. Alternatively, the developed image can be transferred to an intermediate transfer member and subsequently transferred to a copy sheet.

After the transfer of the developed image is completed, copy sheet 16 advances to fusing station 19, depicted in FIG. 1 as fusing and pressure rolls, wherein the developed image is fused to copy sheet 16 by passing copy sheet 16 between the fusing and pressure members, thereby forming a permanent image. Photoreceptor 10, subsequent to transfer, advances to cleaning station 17, wherein any toner left on photoreceptor 10 is cleaned therefrom by use of a blade, brush, or other cleaning apparatus.

Figure 2:
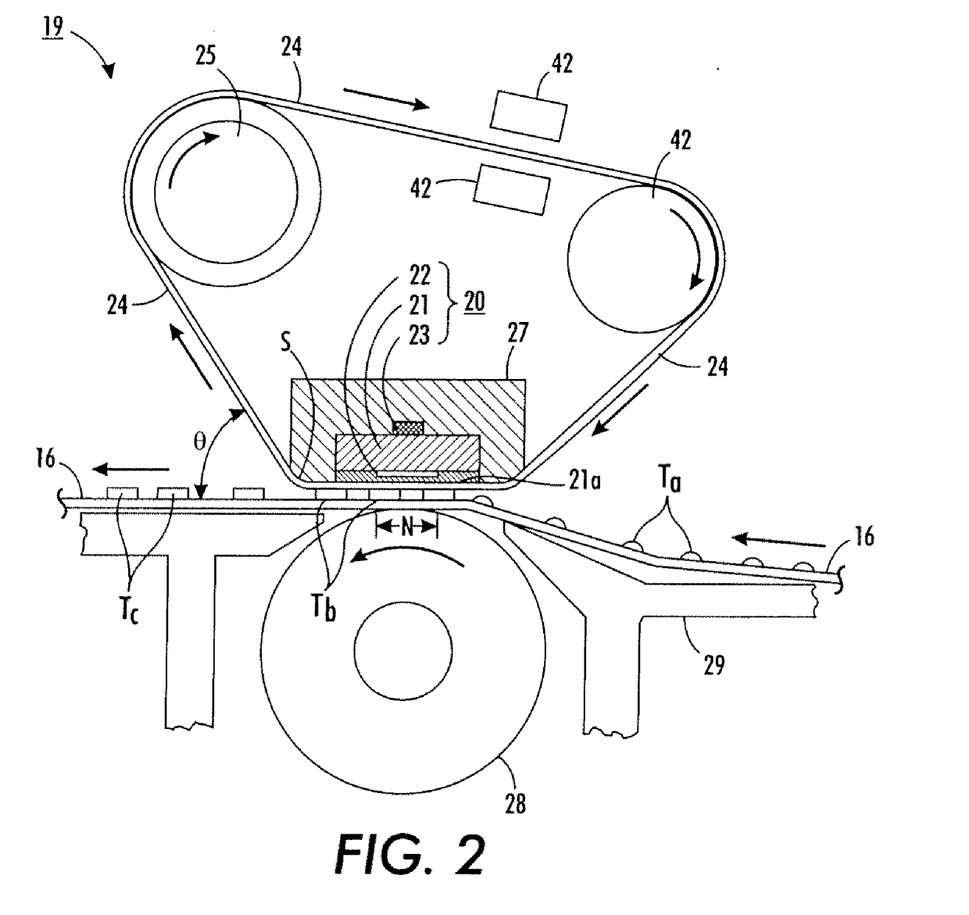
FIG. 2 is a sectional view of a fusing belt and pressure roller in accordance with the present embodiments.

FIG. 2 shows a sectional view of an example of a fusing apparatus 19 according to an embodiment of the present invention. In FIG. 2, a heat resistive film or an image fixing film 24 in the form of an endless belt is trained or contained around three parallel members, that is, a driving roller 25, a follower roller 26 of metal and a low thermal capacity linear heater 20 disposed between the driving roller 25 and the follower roller 26. The follower roller 26 also functions as a tension roller for the fusing belt 24. The fusing belt rotates at a predetermined peripheral speed in the clockwise direction by the clockwise rotation of the driving roller 25. The peripheral speed is the same as the conveying speed of the sheet having an image thereon so that the film is not creased, skewed or delayed.

A pressure roller 28 has a rubber elastic layer with parting properties, such as silicone rubber or the like, and is press-contacted to the heater 20 with the bottom travel of the fusing belt 24 therebetween. The pressure roller is pressed against the heater at the total pressure of 4-7 kg by an urging means (not shown). The pressure roller rotates co-directionally, that is, in the counterclockwise direction, with the fusing belt 24. In the present embodiments, the protective outer layer can be coated on the fuser belt and/or on the pressure roller.

The heater 20 is in the form of a low thermal capacity linear heater extending in a direction crossing with the film 24 surface movement direction (film width direction). It comprises a heater base 27 having a high thermal conductivity, a heat generating resistor 22 generating heat upon electric power supply thereto, and a temperature sensor 23, and is mounted on a heater support 21 having high thermal conductivity.

The heater support 21 supports the heater 20 with thermal insulation on an image fixing apparatus and is made from high heat durability resin such as PPS (polyphenylene sulfide), PAI (polyamideimide), PI (polyimide), polyaramide, polyphthalamide, polyketones, PEEK (polyether ether ketone) or liquid crystal polymer material, or a compound material of such resin material and ceramics, metal, glass or the like material.

An example of the heater base 27 is in the form of an alumina plate having a thickness of 1.0 mm, a width of 10 mm and a length of 240 mm comprised of a high conductivity ceramic material.

The heat generating resistor material 22 is applied by screen printing or the like along a longitudinal line substantially at the center, of the bottom surface of the base 27. The heat generating material 22 is, for example, Ag/Pd (silver palladium), Ta2N or another electric resistor material having a thickness of approximately 10 microns and a width of 1-3 mm. It is coated with a heat resistive glass 21a in the thickness of approximately 10 microns, as a surface protective layer. A temperature sensor 23 is applied by screen printing or the like substantially at a center of a top surface of the base 27 (the side opposite from the side having the heat generating material 22). The sensor is made of Pt film having low thermal capacity. Another example of the temperature sensor is a low thermal capacity thermistor contacted to the base 27.

The linear or strip heater 22 is connected with the power source at the longitudinal opposite ends, so that the heat is generated uniformly along the heater. The power source in this example provides AC 100 V, and the phase angle of the supplied electric power is controlled by a control circuit (not shown) in accordance with the temperature detected by the temperature detecting element 23.

A film position sensor 42 in the form of a photocoupler is disposed adjacent to a lateral end of the film 24. In response to the output of the sensor, the roller 26 is displaced by a driving means in the form of a solenoid (not shown), so as to maintain the film position within a predetermined lateral range.

Upon an image formation start signal, an unfixed toner image is formed on a recording material at the image forming station. The copy sheet 16 having an unfixed toner image Ta thereon is guided by a guide 29 to enter between the fusing belt 24 and the pressure roller 28 at the nip N (fixing nip) provided by the heater 20 and the pressure roller 28. Copy sheet 16 passes through the nip between the heater 20 and the pressure roller 28 together with the fusing belt 24 without surface deviation, crease or lateral shifting while the toner image carrying surface is in contact with the bottom surface with the fusing belt 24 moving at the same speed as copy sheet 16.

The heater 20 is supplied with electric power at a predetermined timing after generation of the image formation start signal so that the toner image is heated at the nip so as to be softened and fused into a softened or fused image Tb.

Fusing belt 24 is sharply bent at an angle theta of, for example, about 45 degrees at an edge S (the radius of curvature is approximately 2 mm), that is, the edge having a large curvature in the heater support 21. Therefore, the sheet advanced together with the film 24 in the nip is separated by the curvature from the fusing belt 24 at edge S. Copy sheet 16 is then discharged to the sheet discharging tray. By the time copy sheet 16 is discharged, the toner has sufficiently cooled and solidified and therefore is completely fixed (toner image Tc).

In this embodiment, heat generating element 22 and base 27 of heater 20 have low thermal capacity. In addition, heater element 22 is supported on support 21 through thermal insulation. The surface temperature of heater 20 in the nip quickly reaches a sufficiently high temperature, which is necessary in order to fuser, the toner. Also, a stand-by temperature control is used to increase the temperature of the heater 20 to a predetermined level. Therefore, power consumption can be reduced, and rise in temperature can be prevented.

The fusing belt is in contact with the heater. The distance between the outer layer of the fusing belt and the heater is preferably from about 0.5 mm to about 5.0 mm. Similarly, the distance between the fusing belt and the grounded rollers 25 and 26 is not less than about 5 mm and is, for example, from about 5 to about 25 mm. These distances prevent leakage of the charge applied to the copy sheet 16 by an image (not shown) forming station from leaking to the ground through the copy sheet 16. Therefore, possible deterioration of image quality due to improper image transfer can be avoided, or minimized.

In another embodiment of the invention, the fusing belt may be in the form of a sheet. For example, a non-endless film may be rolled on a supply shaft and taken out to be wrapped on a take-up shaft through the nip between the heater and the pressure roller. Thus, the film may be fed from the supply shaft to the take-up shaft at the speed, which is equal to the speed of the transfer material, reference U.S. Pat. No. 5,157, 446, the disclosure of which is hereby incorporated by reference in its entirety.

Figure 3:
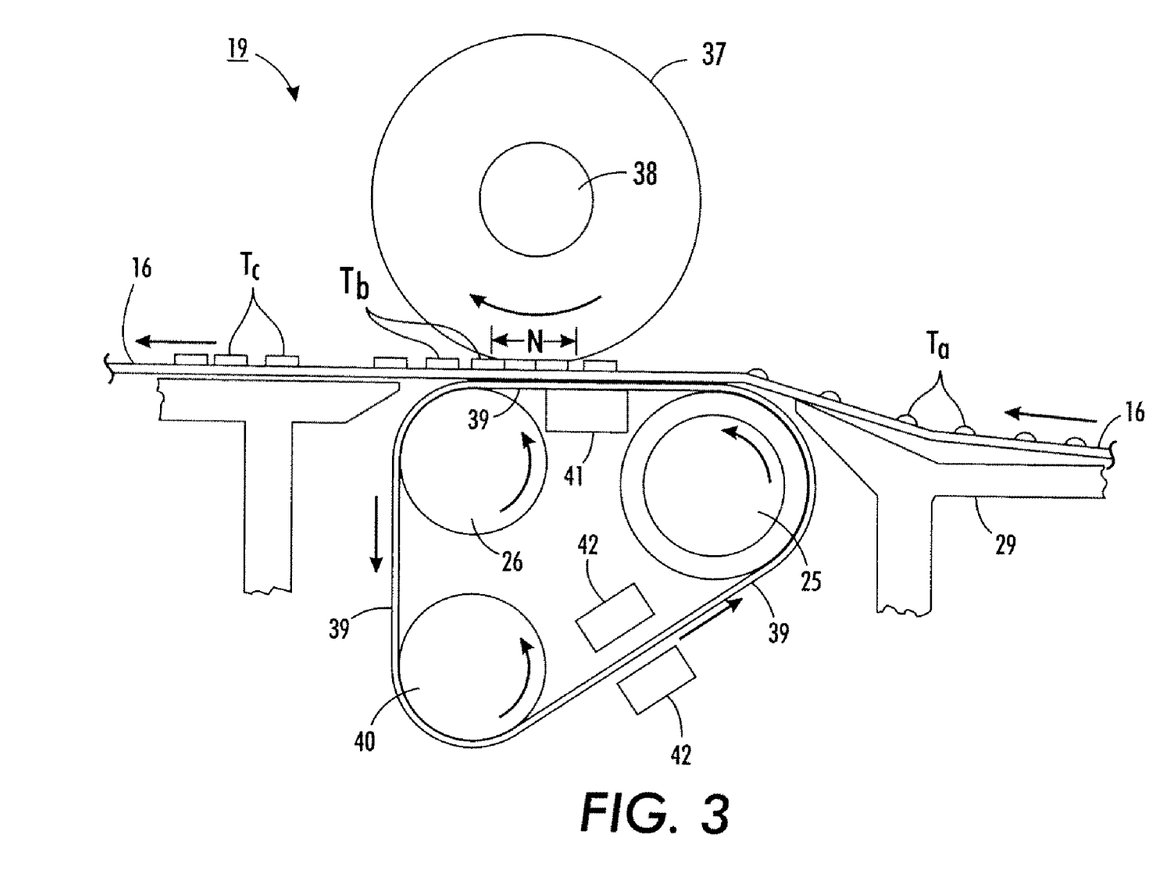
FIG. 3 is a sectional view of a pressure belt and fuser roller in accordance with the present embodiments.

Another embodiment is depicted in FIG. 3, wherein the fuser member is in the form of a fuser roller 37 having internal heater 38 positioned inside the fuser member. In an optional embodiment, the heating member 38 can be positioned on the outside of the fusing member. Pressure belt 39 cycles around rollers 25, 26, and 40. In this alternative configuration, the toner or other marking material is fused to the copy substrate 16 by fuser roller 37. The load on pad 41 is approximately 1.7 kgf. In embodiments, the protective outer layer can be coated on the fuser roller and/or on the pressure belt.

Figure 4:
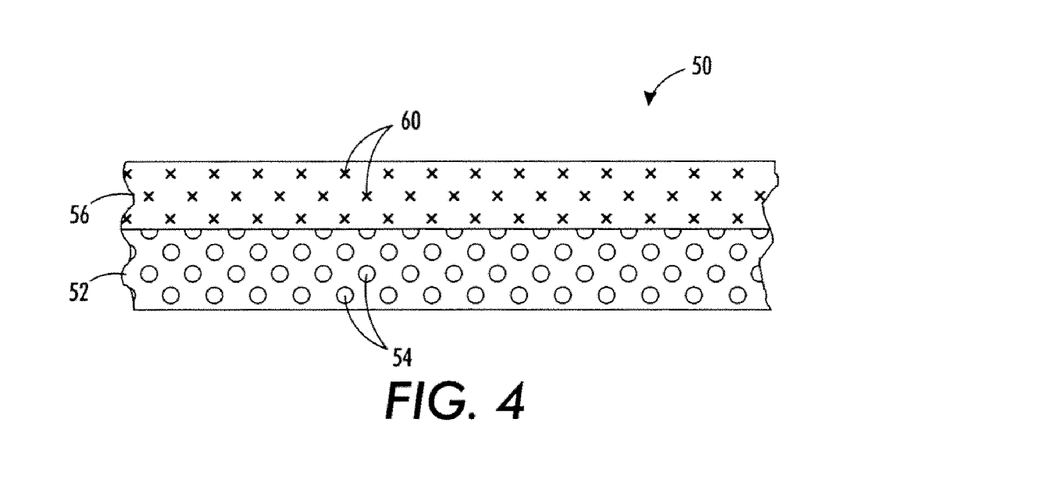
FIG. 4 is a schematic illustration of a fuser component having a two-layer configuration in accordance with the present embodiments.

The fusing component of the present invention can be comprised of various different configurations. In one embodiment of the invention, the fusing component 50 is of a two-layer configuration as shown in FIG. 4. It is understood that this and other configurations herein, can be used on any fusing component that operates in and/or generates high heat. In this embodiment, the fusing component 50 comprises substrate 52 having optional fillers 54 dispersed or contained therein. Positioned over the substrate is the protective outer layer 56 having the phosphonitrilic trimer 60 cross-linked or contained therein. The embodiments also provide for a three layer configuration in which an outer release layer may be positioned over the protective outer layer or that an adhesive or other intermediate layer or layers may be present between the substrate and the protective outer layer.

Examples of suitable substrate materials include in the case of roller or film-type substrates, metals such as aluminum, stainless steel, steel, nickel and the like. In the case of film-type substrates, suitable substrates include high temperature plastics that are suitable for allowing a high operating temperature (i.e., greater than about 80° C., preferably greater than 200° C.), and capable of exhibiting high mechanical strength. In embodiments, the plastic has a flexural strength of from about 2,000,000 to about 3,000,000 psi, and a flexural modulus of from about 25,000 to about 55,000 psi.

Plastics possessing the above characteristics and which are suitable for use as the substrate for the fuser members include epoxy; polyphenylene sulfide such as that sold under the tradenames FORTRON available from Hoechst Celanese, RYTON R-4 available from Phillips Petroleum, and SUPEC available from General Electric; polyimides such as polyamideimide sold under the tradename TORLON 7130 available from Amoco; polyketones such as those sold under the tradename KADEL E1230 available from Amoco, polyether ether ketone sold under the tradename PEEK 450GL30 from Victrex, polyaryletherketone, and the like; polyamides such as polyphthalamide sold under the tradename AMODEL available from Amoco; polyethers such as polyethersulfone, polyetherimide, polyaryletherketone, and the like; polyparabanic acid; and the like; liquid crystalline resin (XYDAR) available from Amoco; ULTEM available from General Electric; ULTRAPEK available from BASF; and the like, and mixtures thereof. Other suitable substrate materials include fluoroelastomers such as those sold under the tradename VITON from DuPont; silicone rubbers, and other elastomeric materials. The substrate may also comprise a mixture of any of the above materials.

The substrate as a film, sheet, belt, or the like, has a thickness of from about 25 to about 250, or from about 60 to about 100 micrometers.

The protective outer layer material is suitable for allowing a high operating temperature. For example, in embodiments the protective outer layer material can operate in a temperature greater than about 80° C., or greater than about 200° C. In more specific embodiments, the protective outer layer material can operate in a temperature from about 150° C. to about 400° C., or from about 200° C. to about 350° C. As a result, the fuser components having an outer layer or coating of the protective material are capable of exhibiting high mechanical strength and optionally possessing tailored electrical properties.

The fusing component employed for the present invention can be of any suitable configuration. Examples of suitable configurations include a sheet, a film, a web, a foil, a strip, a coil, a cylinder, a drum, a roller, an endless strip, a circular disc, a belt including an endless belt, an endless seamed flexible belt, an endless seamless flexible belt, an endless belt having a puzzle cut seam, and the like.

Optionally, any known and available suitable adhesive layer may be positioned between the protective outer layer and the substrate, and/or between the protective outer layer and the outer release layer. Examples of suitable adhesives include silanes such as amino silanes (such as, for example, A1100 from OSI Specialties, Friendly West Virginia), titanates, zirconates, aluminates, and the like, and mixtures thereof. In an embodiment, an adhesive in from about 0.25 to about 10 percent solution, can be wiped on the substrate. The adhesive layer can be coated on the substrate, or on the polyimide outer layer, to a thickness of from about 2 to about 2,000 nanometers, or from about 2 to about 500 nanometers. The adhesive can be coated by any suitable, known technique, including spray coating or wiping.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The example set forth herein below and is illustrative of different compositions and conditions that can be used in practicing the present embodiments. All proportions are by weight unless otherwise indicated. It will be apparent, however, that the embodiments can be practiced with many types of compositions and can have many different uses in accordance with the disclosure above and as pointed out hereinafter.

Example 1

Preparation of the Phosphonitrilic Trimer:

Hexakis(methoxyethylamino)tricyclophosphene (HMEAT) was prepared by adding 10.04 g (28.9 mmol) of phosphonitrilic chloride trimer, along with 200 mL of toluene and 100 mL of triethylamine into a 1 L round bottom flask. The solution was stirred until all solids had dissolved, at which point 26.01 g (346 mmol) of 2-methoxyethylamine was added slowly. This produced a white precipitate almost immediately in the solution. The sample was allowed to reflux for 4 days. The solution was then cooled to room temperature and the solid was filtered off and washed with toluene. The organics were combined and evaporated of solvent and excess base under reduced pressure, leaving the product (13.61 g; 81.3% yield) as a yellow gel. $^1$H (500 MHz, THF-$d_8$) δ 3.45 (t, 2H), 3.33 (s, 3H), 3.05 (br s, 2H). $^{31}$P (200 MHz, CD$_2$Cl$_2$) δ 18.15. The reaction is shown as follows:

The cross-linking properties of the molecule were investigated by preparing a formulation composed of HMEAT and a resin. The solution for film preparation comprised a 60:40 mixture (by weight) of HMEAT and JONCRYL 587 polyol (available from BASF Corp. (Florham Park, N.J.)) in 1-methoxy-2-propanol (DOWANOL PM, available from The Dow Chemical Co. (Midland, Mich.)). NACURE XP-357 acid catalyst (available from King Industries, Inc. (Norwalk, Conn.)) was also added to accelerate the cross-linking (1.0 wt % total solids). The solution was coated on a glass plate using a 5 mil bird bar and dried in a convection oven at 185° C. for 1 hour and resulting in about 30 μm film.

The average hardness of the cured film, analyzed using a nanoindenter, was determined to be 40±2 MPa, which is harder than some commercially available plastics (see Table 1). In addition, the film demonstrated no degradation in the presence of concentrated hydrochloric acid (12.1 N). In fact, concentrated nitric acid (15.8 N) was required to remove the film from the glass substrate.

TABLE 1

| POLYMER | AVERAGE HARDNESS (MPa) |
|---|---|
| 60:40 HMEAT/JONCRYL 587 | 40 |
| HD Polyethylene | 32 |
| LD Polyethylene | 10 |
| Polystyrene | 34 |
| Ethylene Vinyl Acetate | 10-20 |

Figure 5:
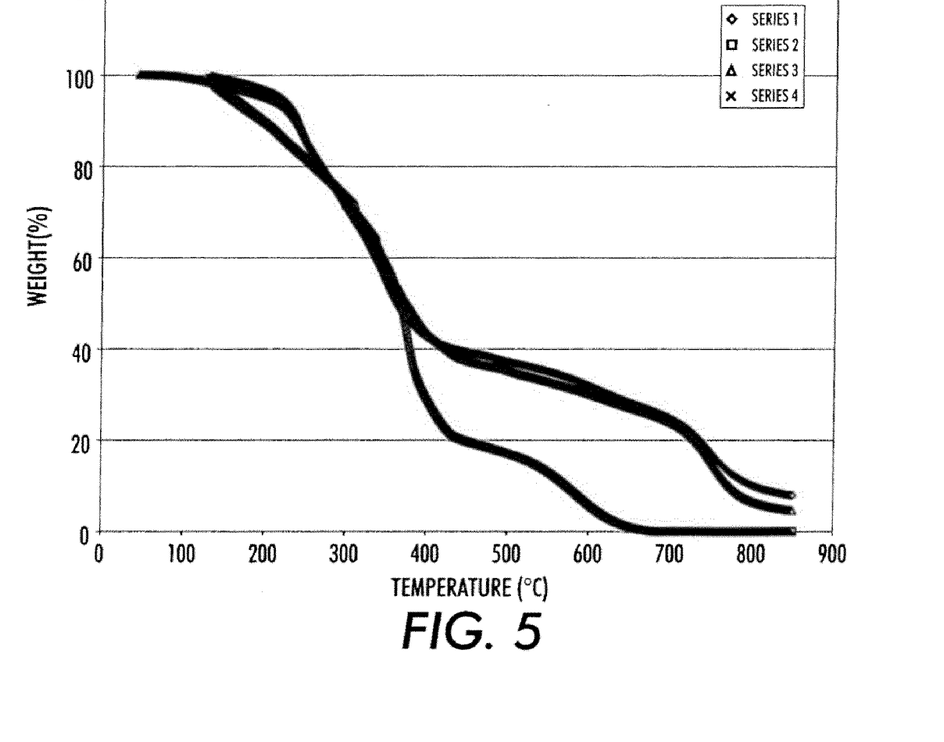
FIG. 5 is a graph illustrating high resistance to thermal degradation exhibited by an outer coating in accordance with the present embodiments.

The thermal stability of a film prepared from the mixture above was compared to that from a mixture of 60:40 CYMEL 303/JONCRYL 587 by thermogravimetric analysis (TGA). As shown in FIG. 5, analysis showed that both samples began to degrade after 200° C. However, at 600° C. almost all of the CYMEL 303/JONCRYL 587 film (bottom two lines represented by square and x) had decomposed, while nearly 40% of the HMEAT/JONCRYL 587 film (top two lines represented by diamond and square) remained intact. In fact, a small amount of the HMEAT/JONCRYL 587 film is still present at 800° C.

FIG. 5 shows thermogravimetric analysis plots of 60:40 CYMEL 303/JONCRYL 587 as compared to HMEAT/JONCRYL 587. As can be seen, the inventive film exhibited much higher resistance to thermal degradation than the control sample.

In summary, the inventors of the present disclosure have prepared a novel phosphonitrilic trimer which has six alkoxyalkyl groups that facilitate cross-linking with a film-forming resin in the presence of an acid catalyst to form a protective coating. The inventive coating shows greater thermal stability than a formulation composed of a commercially available organic melamine and polyol. In addition, the present embodiments provide a film that is resistant to concentrated hydrochloric acid and has an average hardness greater than commonly known polymers.

All the patents and applications referred to herein are hereby specifically, and totally incorporated herein by reference in their entirety in the instant specification.

It will be appreciated that several of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A composition comprising a resin, an acid catalyst and a compound having the following structure:

wherein $R_i$ and $R_{ii}$ are independently selected from the group consisting of alkyl groups and derivatives thereof.

2. The compound of claim 1 having a molecular weight (Mw) of from about 300 to about 900 g/mol.

3. The compound of claim 2 having a molecular weight (Mw) of from about 500 to about 700 g/mol.

4. The composition of claim 1, wherein the acid catalyst is selected from the group consisting of p-toluenesulfonic acid, dinonylnaphthalenesulfonic acid, dinonylnaphthalenedisulfonic acid, dodecylbenzenesulfonic acid, and mixtures thereof.

5. The composition of claim 1, wherein the resin comprises thermoplastic or thermosetting resins selected from the group consisting of polycarbonates, polyesters, polyurethanes, polystyrenes, polyarylethers, polyarylsulfones, polysulfones, polyethersulfones, polyphenylene sulfides, polyvinyl acetate, polyacrylates, polyvinyl acetals, polyamides, polyimides, amino resins, phenolic resins, phenoxy resins, epoxy resins, phenylene oxide resins, polystyrene and acrylonitrile copolymers, vinyl acetate copolymers, acrylate copolymers, alkyd resins, styrene-butadiene copolymers, styrene-alkyd resins, polyvinylcarbazole, and mixtures thereof.

6. The composition of claim 5, wherein the resin is selected from the group consisting of acrylic polyol, polyether polyol, polyester polyol, and mixtures thereof.

7. The composition of claim 1, wherein the compound is present in an amount of from about 5 percent to about 95 percent by weight of the total weight of the composition.

8. The composition of claim 7, wherein the compound is present in an amount of from about 50 percent to about 75 percent by weight of the total weight of the composition.

9. The composition of claim 1, wherein the compound is in gelatinous form.

10. The composition of claim 1, wherein the compound is miscible in organic solvents.

11. A composition comprising a resin cross-linked with a compound having the following structure:

wherein $R_i$ and $R_{ii}$ are independently selected alkyl groups or derivatives thereof.

12. The composition of claim 11, wherein the resin comprises thermoplastic and thermosetting resins selected from the group consisting of polycarbonates, polyesters, polyurethanes, polystyrenes, polyarylethers, polyarylsulfones, polysulfones, polyethersulfones, polyphenylene sulfides, polyvinyl acetate, polyacrylates, polyvinyl acetals, polyamides, polyimides, amino resins, phenolic resins, phenoxy resins, epoxy resins, phenylene oxide resins, polystyrene and acrylonitrile copolymers, vinyl acetate copolymers, acrylate copolymers, alkyd resins, styrene-butadiene copolymers, styrene-alkyd resins, polyvinylcarbazole, and mixtures thereof.

13. The composition of claim 12, wherein the resin is selected from the group consisting of acrylic polyol, polyether polyol, polyester polyol, and mixtures thereof.

14. The composition of claim 11 having a substantially higher resistance to thermal degradation as compared to a composition without the compound.

15. The composition of claim 11, wherein the resin is present in an amount of from about 5 percent to about 95 percent by weight of the total weight of the composition.

16. The composition of claim 11, wherein the resin is present in an amount of from about 25 percent to about 50 percent by weight of the total weight of the composition.

17. The composition of claim 11, wherein a ratio of the compound to the resin in the composition is from about 0.5 to about 3.

* * * * *